United States Patent
Hill et al.

(10) Patent No.: US 8,808,631 B2
(45) Date of Patent: Aug. 19, 2014

(54) CENTRALIZED, TIME-SHARED VAPOR STERILIZATION SYSTEM

(75) Inventors: Aaron L. Hill, Madison, OH (US); Thaddeus J. Mielnik, Concord, OH (US)

(73) Assignee: American Sterilizer Company, Mentor, OH (US)

( * ) Notice: Subject to any disclaimer, the term of this patent is extended or adjusted under 35 U.S.C. 154(b) by 261 days.

(21) Appl. No.: 13/296,766

(22) Filed: Nov. 15, 2011

(65) Prior Publication Data

US 2012/0134881 A1     May 31, 2012

Related U.S. Application Data

(60) Provisional application No. 61/418,015, filed on Nov. 30, 2010.

(51) Int. Cl.
*A61L 2/20* (2006.01)
*A23L 3/00* (2006.01)
*B65B 55/10* (2006.01)

(52) U.S. Cl.
CPC .............. *A61L 2/208* (2013.01); *A23L 3/001* (2013.01); *A61L 2202/15* (2013.01); *B65B 55/10* (2013.01); *A23L 3/003* (2013.01); *A61L 2202/14* (2013.01)
USPC ............................ 422/111; 422/108; 422/292

(58) Field of Classification Search
USPC .......................................... 422/111, 108, 292
See application file for complete search history.

(56) References Cited

U.S. PATENT DOCUMENTS

| | | | |
|---|---|---|---|
| 3,338,663 A | 3/1965 | Beecher et al. | 422/295 |
| 4,843,867 A | 7/1989 | Cummings | 73/23 |
| 5,168,905 A | 12/1992 | Phallen | 141/1 |
| 6,445,969 B1 | 9/2002 | Kenney et al. | 700/108 |
| 6,481,468 B1 | 11/2002 | Taggart | 141/85 |
| 6,953,549 B2 | 10/2005 | Hill et al. | 422/30 |
| 7,186,374 B2 | 3/2007 | Zelina et al. | 422/28 |
| 7,361,304 B2 | 4/2008 | McVey et al. | 422/28 |
| 2004/0112713 A1 | 6/2004 | Haan et al. | 198/419.2 |
| 2007/0253859 A1 | 11/2007 | Hill | 422/3 |

FOREIGN PATENT DOCUMENTS

| | | | | |
|---|---|---|---|---|
| WO | WO 02/092140 | 11/2002 | | A61L 2/20 |
| WO | WO 2005/060385 | 7/2005 | | |
| WO | WO 2006/031957 | 3/2006 | | A61L 2/20 |

*Primary Examiner* — Sean E Conley
(74) *Attorney, Agent, or Firm* — Kusner & Jaffe; Michael A. Centanni

(57) ABSTRACT

A system for conveying a sterilant vapor to a plurality of processing lines having articles moving therealong. The system includes a central source of a sterilant vapor. A conveying device is provided for conveying a sterilant vapor from the central source to a plurality of processing lines. A plurality of sensing devices are provided for sensing a plurality of operational parameters associated with the system and the plurality of processing lines. A controller is provided for receiving signals from the plurality of sensing devices. The controller is programmed to monitor continuously the plurality of sensing devices to determine if an event indicative of a malfunction has occurred with respect to the system or the plurality of processing lines. The controller is programmed to adjust the operation of the system in response to the event to maintain uninterrupted operation of one or more of the plurality of processing lines.

22 Claims, 3 Drawing Sheets

CENTRALIZED, TIME-SHARED VAPOR STERILIZATION SYSTEM

RELATED APPLICATION

This application claims the benefit of U.S. Provisional Application No. 61/418,015, filed Nov. 30, 2010, which is fully incorporated herein by reference.

FIELD OF THE INVENTION

The present invention relates generally to the sterilization of articles, and more particularly, to a system for supplying a vapor sterilant from a central source to a plurality of processing lines having articles moving therealong and a method of operating the same.

BACKGROUND OF THE INVENTION

In the food industry, facilities for packaging products, such as food, beverages, and the like, are known to include a plurality of processing lines therein. The processing lines are designed to place the product into an article, such as a container. The containers typically are sterilized prior to being filled with a desired product.

Some filling lines use containers that are made from a flat sheet of web material. The web material typically is made from layers of paper cardboard, plastic and foil that are laminated together. Prior to forming the web material into a container, the web material is dipped into a bath of liquid hydrogen peroxide, dried and formed into the container. Dipping the containers into a high concentrate of liquid hydrogen peroxide (typically at 35% concentration) may result in high residual levels of hydrogen peroxide in the material.

Other processing lines use containers that have a closed end and an open end. The open end of each container is oriented upward to allow liquid peroxide to be sprayed into the container. The container is then rinsed with sterile water. To drain the container, the container is inverted so that the open end of the container is oriented downward. The container is then inverted again so that the open end of the container is then oriented upward to allow for filling with a beverage.

It is desirable to sterilize the containers in a manner that does not require repeated re-orienting of the containers and that reduces the amount of residual peroxide on the container. By simplifying the sterilization of the containers and reducing the amount of residual peroxide on the containers, the time required to sterilize the containers can be reduced.

Recently, the food industry has begun to use hydrogen peroxide vapor to sterilize containers. Hydrogen peroxide vapor has proven to be efficient at sterilizing the containers quickly and at leaving small amounts of residual peroxide on the containers. Some systems provide the hydrogen peroxide vapor from a central source to the plurality of processing lines to sterilize the containers moving therealong. In these systems, the hydrogen peroxide vapor is typically conveyed from the central source simultaneously to each processing line at the same concentration and at the same flow rate.

One problem with a central source of hydrogen peroxide vapor arises when a malfunction occurs along one processing line. A malfunction along one processing line will cause all the processing lines to be shut down until the malfunction is repaired. As can be appreciated, if all the processing lines in the facility are shut down, the output of the facility is reduced and the operating cost of the facility increases. It is therefore desirable to have a system and method for providing a sterilant vapor to one or more processing lines when an event indicative of a malfunction is detected with the system or one or more of the plurality of processing lines.

The present invention provides a system for providing a sterliant vapor to a plurality of processing lines having articles moving therealong. The system includes a plurality of sensors associated with the plurality of processing lines which sensors provide signals indicative of the operation of the system and the plurality of processing lines. A controller is provided for monitoring continuously the plurality of sensors. The controller is programmed to monitor the plurality of sensors to detect an event (or events) that is indicative of a malfunction with the system or with one or more of the plurality of processing lines. If an event is detected, the controller adjusts the operation of the system and/or the plurality of processing lines to provide uninterrupted operation of one or more of the plurality of processing lines.

SUMMARY OF THE INVENTION

In accordance with a preferred embodiment of the present invention, there is provided a system for conveying a sterilant vapor to a plurality of processing lines having articles moving therealong. The system includes a central source of a sterilant vapor. A conveying device is provided for conveying a sterilant vapor from the central source to a plurality of processing lines. A plurality of sensing devices are provided for sensing a plurality of operational parameters associated with the system and the plurality of processing lines. A controller is provided for receiving signals from the plurality of sensing devices. The controller is programmed to monitor continuously the plurality of sensing devices to determine if an event indicative of a malfunction has occurred with respect to the system or the plurality of processing lines. The controller is programmed to adjust the operation of the system in response to the event to maintain uninterrupted operation of one or more of the plurality of processing lines.

An advantage of the present invention is a system for providing a sterilant vapor to a plurality of processing lines from a central source of a sterilant vapor.

Another advantage of the present invention is a system, as described above, that includes a plurality of sensors that continuously monitor the operation of the plurality of processing lines.

Yet another advantage of the present invention is a system, as described above, wherein a controller is programmed to detect an event indicative of a malfunction with the system or one or more of the plurality of processing lines.

Another advantage of the present invention is a system, as described above, wherein the controller adjusts operation of the system in response to a detected event to provide uninterrupted supply of the sterilant vapor to one or more of the plurality of processing lines.

Yet another advantage of the present invention is a system, as described above, wherein the controller adjusts the output of the central source in response to an event (or events) indicative of a malfunction with the system or one or more of the plurality of processing lines.

Still another advantage of the present invention is a system, as described above, wherein the controller adjusts the concentration of sterilant vapor from the central source in response to an event (or events) indicative of a malfunction with the system or one or more of the plurality of processing lines.

Another advantage of the present invention is a system, as described above, wherein the controller adjusts the flow rate of sterilant vapor from the central source in response to an event (or events) indicative of a malfunction with the system or one or more of the plurality of processing lines.

Still another advantage of the present invention is a system, as described above, wherein the controller adjusts the temperature of the sterilant vapor from the central source in response to an event (or events) indicative of a malfunction with the system or one or more of the plurality of processing lines.

Yet another advantage of the present invention is a system, as described above, wherein the controller adjusts the speed of one or more of the plurality of processing lines in response to an event (or events) indicative of a malfunction with the system or one or more of the plurality of processing lines.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
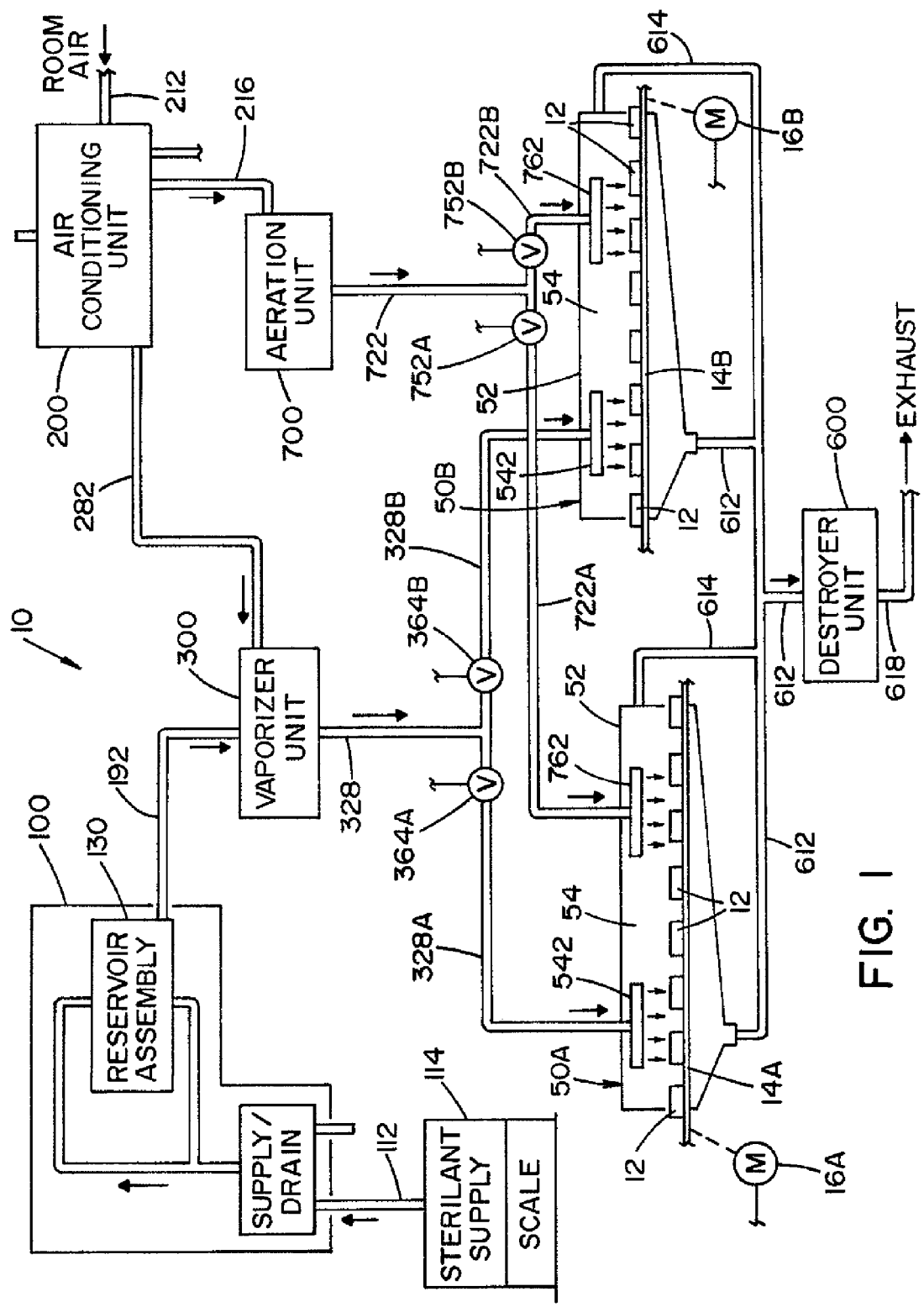
FIG. 1 is a drawing schematically illustrating a sterilant supply system for supplying a vapor sterilant to a plurality of processing lines, illustrating a preferred embodiment of the present invention.

Referring now to the drawings wherein the showings are for the purpose of illustrating a preferred embodiment of the invention only, and not for the purpose of limiting the same, FIG. 1 shows a sterilant supply system 10 for providing a sterilant vapor to a plurality of processing lines having containers 12 moving therealong. Sterilant supply system 10 will be described with respect to sterilizing containers moving along a plurality of processing lines in a food packaging facility. However, it is appreciated that the present invention may find advantageous application in other systems for supplying a sterilant vapor to a plurality of processing lines having articles, such as medical instruments, moving therealong.

In the embodiments shown, conveyors 14A, 14B represent two (2) processing lines associated with system 10. Conveyor 14A represents a portion of a first processing line for containers 12. Conveyor 14B represents a portion of a second processing line for containers 12. A first motor 16A is provided for causing conveyor 14A to move containers 12 therealong. A second motor 16B is provided for causing conveyor 14B to move containers 12 therealong.

Conveyors 14A, 14B extend through decontamination chambers 50A, 50B. System 10 conveys the sterilant vapor to the portion of conveyors 14A, 14B that is disposed within decontamination chambers 50A, 50B. Each of decontamination chambers 50A, 50B has an enclosure or housing 52. Housing 52 defines a space or region 54 through which containers 12 to be sterilized are conveyed by conveyors 14A, 14B. After containers 12 are sterilized by system 10, containers 12 are conveyed to a filling station (not shown), wherein containers 12 are filled with a beverage or some other product.

Broadly stated, sterilant supply system 10, according to the present invention, is comprised of a sterilant supply unit, an air conditioning unit, a vaporizer unit, a destroyer unit and an aeration unit. The foregoing components are described in detail in U.S. patent application Ser. No. 11/741,299, hereby incorporated by reference. In the embodiment shown, sterilant supply system 10 includes a single sterilant supply unit 100, a single air conditioning unit 200, a single vaporizer unit 300, a single destroyer unit 600 and a single aeration unit 700. It is contemplated that sterilant supply system 10 may convey a sterilant vapor to more than two (2) processing lines. However, sterilant supply system 10 will be described below in reference to conveying a sterilant vapor to two (2) processing lines in order to simplify the description of the present invention.

Referring now to FIG. 1, sterilant supply unit 100 is shown. A supply line 112 connects sterilant supply unit 100 to an external supply 114 of liquid sterilant. A reservoir assembly 130 is provided to allow continuous, uninterrupted flow of sterilant to vaporizer unit 300. A vaporizer feed line 192 is connected at one end to reservoir assembly 130 and at another end to vaporizer unit 300.

Air conditioning unit 200 is provided to condition, i.e., to filter and to dry air used in vaporizer unit 300, and to filter air used by aeration unit 700. An air inlet conduit 212 has a first end that communicates with the environment, namely room air, and another end that is connected to air conditioning unit 200. A first air supply line 282 is connected at one end to air conditioning unit 200 and at another end to vaporizer unit 300. A second air supply line 216 is connected at one end to air conditioning unit 200 and at another end to aeration unit 700.

Figure 2:
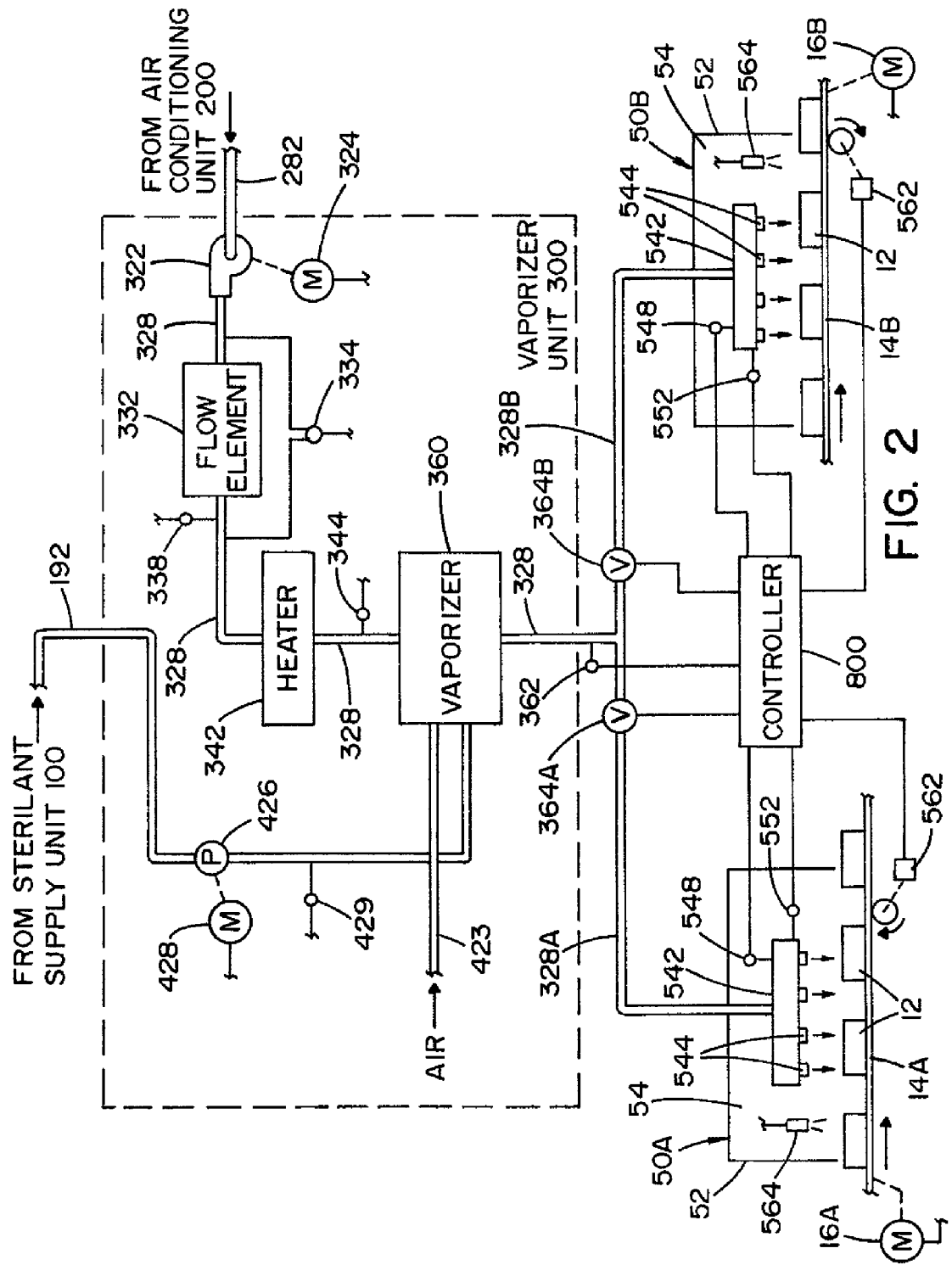
FIG. 2 is a drawing pictorially illustrating a vaporizer unit of the sterilant supply system shown in FIG. 1.

As shown in FIG. 2, vaporizer unit 300 is connected to vaporizer feed line 192 from sterilant supply unit 100, and is connected to air line 282 from air conditioning unit 200. Vaporizer unit 300 is comprised of a blower 322, a flow element 332 for measuring airflow, a heater 342 and a vaporizer 360.

Blower 322 is disposed in air supply line 282 from air conditioning unit 200. Blower 322 is driven by a motor 324. Motor 324 is preferably a variable speed motor, wherein the output of blower 322 can be controlled to increase or decrease air flow therethrough. When in operation, blower 322 draws air through air conditioning unit 200 wherein the air is dried and filtered. In the embodiment shown, the outlet of blower 322 is connected to a conduit 328. A flow element 332 is disposed within conduit 328 to measure air flow through conduit 328. Flow element 332 is preferably a Venturi device. A sensor 334 measures a pressure difference across flow element 332 and provides a signal indicative of the air flow through flow element 332. A Venturi device is preferable because of the high resolution of air flow it can provide and because of the low loss of power for the air flowing therethrough. A temperature sensor 338 is disposed downstream from flow element 332.

Heater 342 is disposed within conduit 328 and is provided to heat the air flowing through conduit 328. Heater 342 is designed to be capable of heating air flowing through conduit 328 up to a temperature high enough to vaporize hydrogen peroxide and high enough to maintain a desired temperature sufficient to prevent condensation in sterilant supply system 10. In one embodiment, heater 342 is capable of heating air flowing through conduit 328 to at least about 105° C. In another embodiment, heater 342 is capable of heating air flowing through conduit 328 to at least 180° C. A temperature sensor 344 is disposed downstream of heater 342. Temperature sensor 344 provides a signal indicative of the temperature of the air flowing through conduit 328.

Vaporizer 360 is disposed within conduit 328 at a location downstream from heater 342. A hydrogen peroxide vapor sensor 362, that provides a signal indicative of the concentration of hydrogen peroxide vapor and water vapor, is disposed within conduit 328 on the outlet of vaporizer 360. Sensor 362 is preferably an infrared (IR) sensor, and more preferably a near infrared (IR) sensor.

A conduit 423 is connected at one end to a source (not shown) of filtered, dry pressurized air and at another end to vaporizer 360. A pump 426, driven by a motor 428, is disposed in sterilant supply line 192 to feed sterilant under pressure into vaporizer 360. Pump 426 is preferably a variable-speed peristaltic pump. Pump 426 is provided to pump sterilant into vaporizer 360 at a selected rate. Motor 428 is preferably a variable speed motor wherein the injection rate of sterilant to vaporizer 360 can be varied by varying the speed of motor 428. A pressure sensor 429 is disposed in sterilant supply line 192, downstream from pump 426. Pressure sensor 429 monitors (and ensures) a proper sterilant injection rate.

As illustrated in FIG. 2, conduit 328 divides into a first branch 328A and a second branch 328B. Vaporizer unit 300 is connected to decontamination chambers 50A, 50B by hydrogen peroxide vapor branch conduits 328A, 328B. A first valve 364A is disposed in first branch 328A to regulate the amount of flow through first branch 328A. A second valve 364B is disposed in second branch 328B to regulate the amount of flow through second branch 328B.

A manifold 542 is mounted to an end of each hydrogen peroxide vapor branch conduits 328A, 328B. Manifold 542 associated with first branch 328A is essentially identical to manifold 542 associated with second branch 328B. Therefore, only manifold 542 associated with first branch 328A will be described, it being understood that such description applies equally to manifold 542 associated with second branch 328B. In the embodiment shown, manifold 542 is disposed within housing 52. Manifold 542 has a plurality of spaced-apart openings or nozzles 544 that communicate with space or region 54 in housing 52 of decontamination chamber 50A. Nozzles 544 are disposed above conveyor 14A to distribute uniformly hydrogen peroxide vapor over containers 12 moving through decontamination chamber 50A.

As shown in FIG. 1, conduits 612, 614 connect enclosure 52 of decontamination chamber 50A to destroyer unit 600. Conduit 612 communicates with region 54 in enclosure 52 through a bottom of enclosure 52. Conduit 614 communicates with region 54 in enclosure 52 through one side of enclosure 52. An outlet conduit 618 fluidly connects destroyer unit 600 to a surrounding environment. Destroyer unit 600 includes a destroyer. The destroyer is basically a catalytic device that is operable to destroy hydrogen peroxide flowing therethrough. In this respect, catalytic destroyers convert the hydrogen peroxide vapor into water and oxygen.

Figure 3:
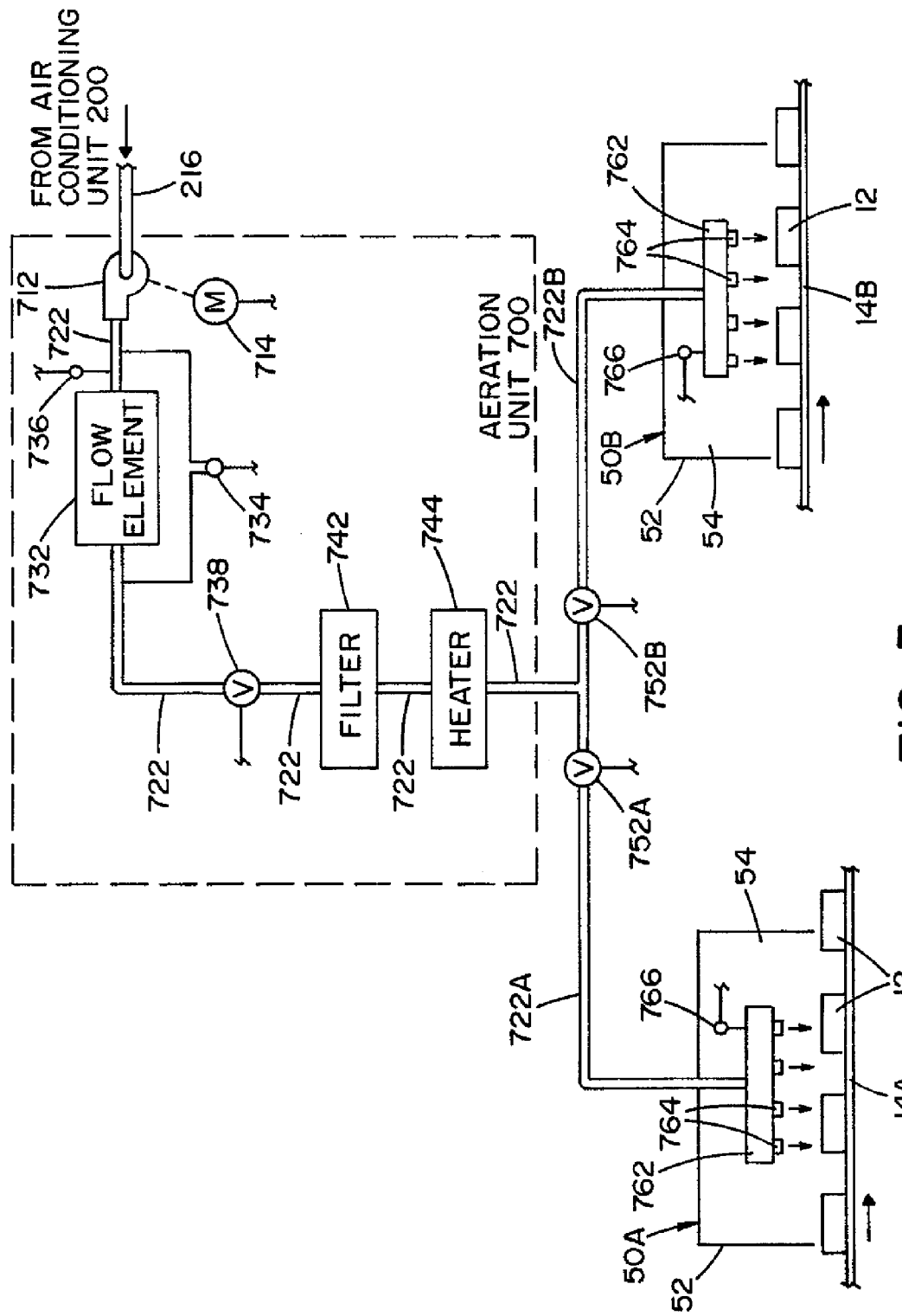
FIG. 3 is a drawing schematically illustrating an aeration unit of the sterilant supply system shown in FIG. 1.

Referring now to FIG. 3, aeration unit 700 is best seen. Aeration unit 700 is connected to second air supply line 216 from air conditioning unit 200. Second air supply line 216 from air conditioning unit 200 supplies filtered air to aeration unit 700. Second air supply line 216 is connected to the inlet side of a blower 712. Blower 712 is driven by a variable-speed motor 714. Blower 712 is disposed within aeration unit 700 to draw air external to system 10 through air conditioning unit 200 and through second air supply line 216. The outlet side of blower 712 is connected to an aeration conduit 722. Aeration conduit 722 extends through aeration unit 700. Downstream from blower 712, a flow element 732 is disposed within aeration conduit 722. In a preferred embodiment, flow element 732 is a Venturi device.

A pressure sensor 734 measures the pressure difference across flow element 732 to provide signals indicative of the flow through aeration conduit 722. A temperature sensor 736 is disposed before (upstream of) flow element 732. Temperature sensor 736 is disposed between blower 712 and flow element 732. A valve 738 is disposed in aeration conduit 722 downstream from flow element 732 to regulate the amount of flow through aeration conduit 722. A filter 742 is disposed downstream from valve 738. Filter 742, preferably a HEPA filter, provides a second filtration of the air flowing through aeration conduit 722. A heater 744 is disposed in aeration conduit 722 downstream from filter 742. Heater 744 is provided to heat the air flowing along conduit 722.

As illustrated in FIG. 3, aeration conduit 722 divides into a first branch 722A and a second branch 722B. Aeration unit 700 is connected to decontamination chambers 50A, 50B by aeration branch conduits 722A, 722B. A first valve 752A is disposed in first branch 722A to regulate the amount of flow through first branch 722A. A second valve 752B is disposed in second branch 722B to regulate the amount of flow through second branch 722B.

A manifold 762 is connected to an end of each aeration branch conduits 722A, 722B. Manifold 762 associated with first branch 722A is essentially identical to manifold 762 associated with second branch 722B. Therefore, only manifold 762 associated with first branch 722A will be described, it being understood that such description applies equally to manifold 762 associated with second branch 722B. In the embodiment shown, manifold 762 is disposed in housing 52 of decontamination chamber 50A. Manifold 762 includes a plurality of nozzles or ports 764 to distribute the filtered and heated air into decontamination chamber 50A. Manifold 762 is disposed above conveyor 14A at a location where conveyor 14A exits decontamination chamber 50A. A temperature sensor 766 is disposed within manifold 762. Aeration unit 700 basically provides heated, filtered air to decontamination chamber 50A to purge hydrogen peroxide vapor from containers 12 on conveyor 14A and to prevent condensation.

According to the present invention, a plurality of sensors are disposed within decontamination chambers 50A, 50B. The plurality of sensors are connected to a controller 800 (described in detail below) to provide signs indicative of the operation of sterilant supply system 10 and conveyors 14A, 14B. The sensors associated with conveyor 14A are essentially identical to the sensors associated with conveyor 14B. Therefore, only the sensors associated with conveyor 14A will be described, it being understood that such description applies equally to the sensors associated with conveyor 14B.

As shown in FIG. 2, a temperature sensor 548 and a hydrogen peroxide vapor sensor 552 are disposed relative to conveyor 14A. In the embodiment shown, temperature sensor 548 and hydrogen peroxide vapor sensor 552 are disposed within manifold 542. Temperature sensor 548 provides a signal indicative of the temperature within manifold 542. Hydrogen peroxide vapor sensor 552 provides a signal indicative of the concentration of hydrogen peroxide vapor and water vapor in manifold 542. Sensor 552 is preferably a near infrared (IR) sensor.

A conveyor sensor 562 is disposed relative to conveyor 14A. Conveyor sensor 562 provides a signal indicative of the movement of conveyor 14A through region 54. For example, conveyor sensor 562 may provide a signal indicative of the speed at which conveyor 14A is moving. In the embodiment shown, sensor 562 includes a wheel that is disposed to be in contact with conveyor 14A. In this respect, movement of conveyor 14A causes the wheel to turn. As the wheel turns, sensor 562 provides a signal indicative of the movement of conveyor 14A. It is also contemplated that sensor 562 may be a conventionally known sensor, e.g., a proximity sensor, that is useful at detecting movement of conveyor 14A through region 54.

An article sensor 564 is disposed relative to conveyor 14A. Article sensor 564 provides a signal indicative of whether containers 12 are moving through region 54. In the embodiment shown, sensor 564 is a conventional proximity sensor that is useful at detecting the presence of an article at a predetermined location in region 54.

Controller 800 receives signals from the various sensors disposed within system 10. In the embodiment shown, controller 800 receives signals from a plurality of sensors associated with sterilant supply system 10 and conveyors 14A, 14B. In particular, controller 800 receives signals from sensors 334, 338, 344, 362, 429, 548, 552, 562, 564, 734, 736, 766. Controller 800 is programmed to monitor constantly the signals from the aforementioned sensors in order to control the operation of system 10 and conveyors 14A, 14B and to determine if an event indicative of a malfunction has occurred with respect to system 10 or conveyors 14A, 14B. If an event indicative of a malfunction is detected, controller 800 is programmed to adjust the operation of system 10 and/or conveyors 14A, 14B to maintain uninterrupted operation of as many processing lines as possible. In particular, based upon the nature of the event detected by controller 800, controller 800 will shut down one or more processing lines and simultaneously adjust the operation of sterilant supply system 10 and/or conveyors 14A, 14B in order to maintain uninterrupted operation of as many processing lines as possible.

Events that are indicative of a malfunction include, but are not limited to: 1) the speed that a processing line is conveying containers 12 is outside of an acceptable speed range; 2) the number of containers 12 that are conveyed along a processing line is outside of an anticipated range; 3) the concentration of hydrogen peroxide vapor that is conveyed to a processing line is outside of an acceptable range; 4) the temperature of the air that is conveyed to a processing line is outside of an acceptable range; 5) the flow rate of the hydrogen peroxide vapor that is conveyed to a processing line is outside of an acceptable range. It is contemplated that other sensors may be placed within system 10 to provide signals indicative of malfunctions other than those listed above.

Controller 800 is programmed to control the air temperature, air flow rate, sterilant temperature and sterilant injection rate in sterilant supply system 10 so that the concentration of hydrogen peroxide vapor conveyed to the first and second processing lines is within a user-defined acceptable range. Controller 800 also controls the speed at which containers 12 move along the first processing line and the second processing line. In particular, controller 800 controls the speed that containers 12 move so that the duration of time that containers 12 are exposed to hydrogen peroxide vapor is sufficient to sterilize containers 12. Controller 800 includes input means for allowing a user to input the user-defined acceptable range for the concentration of hydrogen peroxide vapor.

When using hydrogen peroxide vapor in a sterilization system, it is necessary to prevent the hydrogen peroxide vapor from condensing on the articles to be sterilized. In a steady state, steady flow hydrogen peroxide vapor sterilization process, the sterilant injection rate, the air flow rate and the air temperature must be controlled to prevent condensation. According to one embodiment of the present invention, system 10 is controlled to a desired hydrogen peroxide vapor concentration and temperature, to prevent condensation. In particular, the operation of system 10 is controlled to maintain the concentration of hydrogen peroxide vapor in an air stream at a dew point temperature that is below the temperature of articles to be sterilized. System 10 may be controlled based upon a mathematical model, as described in detail in U.S. patent application Ser. No. 11/741,299.

Controller 800 is also programmed to control the air temperature and the air flow rate in aeration unit 700 so that the air conveyed to each processing line is maintained within a user-defined acceptable flow rate range and within a user-defined acceptable temperature range. Controller 800 includes input means for allowing a user to input the aforementioned user-defined acceptable ranges.

Controller 800 receives signals from sensors 334, 338, 344, 362, 429, 548, 552, 562, 564, 734, 736, 766. Controller 800 also controls the operation of motors 16A, 16B, 324, 428, 714, valves 364A, 364B, 738, 752A, 752B and heaters 342, 744. In particular, controller 800 controls the operation of the foregoing components based on signals received from sensors 334, 338, 344, 362, 429, 548, 552, 562, 564, 734, 736, 766, as described in detail below.

Referring now to the operation of the present invention, controller 800 is programmed to cause system 10 to operate in two (2) different modes of operation, namely: (1) a first, normal mode of operation and (2) a second, event-driven mode of operation. During the first mode of operation, all the processing lines are in full operation such that containers 12 conveyed along the processing lines are sterilized. During the second mode of operation, controller 800 adjusts the operation of system 10 and/or conveyors 14A, 14B, as needed, in response to an event that is indicative of a malfunction with system 10 or conveyors 14A, 14B.

During the first mode of operation, controller 800 controls system 10 such that containers 12 conveyed along a plurality of processing lines are sterilized. In the embodiment shown, containers 12 are conveyed along a first processing line, represented by conveyor 14A, and a second processing line, represented by conveyor 14B. In particular, controller 800 causes valves 364A, 36413 to be in an open position so that hydrogen peroxide vapor is conveyed from sterilant supply system 10 to containers 12 moving along conveyors 14A, 14B.

As set forth above, controller 800 is programmed such that motors 16A, 16B, 324, 428 and heater 342 are controlled based on signals received from sensors 334, 338, 344, 362, 429, 548, 552, 562, 564. In particular, based on the signals from sensor 552, controller 800 controls motor 428 so that the quantity of liquid hydrogen peroxide supplied to vaporizer 360 is sufficient to sterilize containers 12 moving through decontamination chambers 50A, 50B. Controller 800 also controls motor 324 so that the quantity of air moving through vaporizer 360 is sufficient to convey the hydrogen peroxide vapor to containers 12 moving through decontamination chambers 50A, 50B. Based on the signals from temperature sensor 548 in manifold 542, controller 800 controls heater 342 to achieve the air temperature needed to maintain the concentration of hydrogen peroxide vapor in each decontamination chamber 50A, 50B within the user-defined acceptable range. Based on the concentration of hydrogen peroxide vapor in decontamination chambers 50A, 50B, controller 800 causes motors 16A, 16B to move containers 12 along the first and second processing lines at a speed that allows containers 12 to be exposed to hydrogen peroxide vapor for a duration of time sufficient to sterilize containers 12. As noted above, sensor 562 provides a signal indicative of the speed that conveyors 14A, 14B are moving containers 12. Sensor 564 provides an indication of the number of containers 12 that are moving along conveyors 14A, 14B. In this respect, based on signals from sensors 562, 564, controller 800 determines whether the correct number of containers 12 are being conveyed through decontamination chambers 50A, 50B at the correct speed.

In one embodiment of the present invention, controller 800 also controls the air temperature and the air flow rate from aeration unit 700. In this respect, controller 800 controls aeration unit 700 so that the air conveyed to containers 12 moving through decontamination chambers 50A, 50B is within the user-defined acceptable ranges. In this embodiment, controller 800 causes valves 752A, 752B to be in the open position so that warm, sterile air is conveyed from aeration unit 700 to both decontamination chambers 50A, 50B. The warm, sterile air is provided to remove hydrogen peroxide vapor from containers 12 moving through both decontamination chambers 50A, 50B. In particular, based on signals from sensors 736, 734, 766, controller 800 controls motor 714 and heater 744 so that the quantity of air and the temperature of the air conveyed from aeration unit 700 are sufficient to remove the hydrogen peroxide vapor from containers 12 moving through decontamination chambers 50A, 50B.

Residual hydrogen peroxide vapor exits decontamination chambers 50A, 50B through conduits 612, 614. The residual hydrogen peroxide vapor is conveyed to destroyer unit 600 wherein the hydrogen peroxide vapor is reduced to water and oxygen. The water and oxygen are conveyed out of destroyer unit 600 through outlet conduit 618.

As described above, controller 800 thus causes system 10 to operate in a first mode of operation wherein containers 12 moving along conveyors 14A, 14B are sterilized.

During the first mode of operation, controller 800 constantly monitors the various sensors disposed within system 10 to determine if an event indicative of a malfunction has occurred with respect to system 10 or conveyors 14A, 14B. For example, if the concentration of hydrogen peroxide vapor in one decontamination chamber drifts outside of the user-defined acceptable range, sensor 552 will provide a signal to controller 800 that is indicative of such an event. Based on a detected event that is indicative of a malfunction, such as the one described above, controller 800 is programmed to initiate a second, event-driven mode of operation. In general, during the second, event-driven mode of operation controller 800 adjusts the operation of system 10 and/or conveyors 14A, 14B so that as many processing lines as possible remain in operation.

The operation of the present invention with respect to the second mode of operation will be described in detail with respect to an event indicative of a malfunction occurring along the first processing line, i.e., the processing line associated with conveyor 14A. However, it is understood that the following description would apply equally to the detection of an event indicative of a malfunction occurring along the second processing line, i.e., the processing line associated with conveyor 14B.

Upon the detection of an event along the first processing line, controller 800 first determines whether the first processing line must be shut down or if the operation of the first processing line can be "modified" to maintain the first processing line in operation. For example, if the signal to controller 800 indicates that the flow of sterilant vapor to the first processing line is stopped completely, controller 800 may determine that it is necessary to shut down the first processing line. In this respect, controller 800 is programmed to cause valve 364A to move to a closed position such that decontamination chamber 50A is isolated fluidly from vaporizer unit 300. Simultaneously therewith, controller 800 causes motor 16A to stop such that containers 12 cease to move along conveyor 14A, i.e., the first processing line.

However, if the signal to controller 800 indicates that the sterilant vapor conveyed to chamber 50A is outside of the user-defined acceptable range, controller 800 may determine that it is possible to "modify" the operation of the first processing line to continue to sterilize containers 12 moving therealong. For example, if the flow of sterilant vapor to chamber 50A is low, controller 800 may cause motor 16A to reduce the speed that containers 12 move through chamber 50A so that the duration of time that containers 12 are in chamber 50A is sufficient to sterilize containers 12. If the flow of sterilant vapor to chamber 50A is high, controller 800 may cause valve 364A to reduce the flow of sterilant vapor to chamber 50A and/or controller 800 may cause motor 16A to increase the speed that containers 12 move through chamber 50A. It is also contemplated that controller 800 is programmed to modify the operation of the first processing line if other parameters, such as the temperature or the concentration of the sterilant vapor, are outside of the user-defined acceptable range.

Regardless of whether controller 800 shuts down the first processing line, or modifies the operation of the first processing line, controller 800 will continue to monitor the sensors associated with the second processing line. Based on the signals received from the sensors associated with the second processing line, controller 800 causes motors 324, 428 to adjust the output of pump 426 and blower 322 so that articles conveyed along the second processing line, i.e., conveyor 14B, continue to be sterilized. For example, controller 800 is programmed to use the signals from sensor 552 in decontamination chamber 50B to determine if the concentration of hydrogen peroxide vapor supplied to decontamination chamber 50B is within the user-defined acceptable range. If the concentration is outside of the user-defined acceptable range, controller 800 will cause motor 428 to decrease or increase the flow rate of liquid hydrogen peroxide to vaporizer 360. Similarly, controller 800 will cause motor 324 to decrease or increase the flow rate of air to decontamination chamber 50B. Controller 800 will continue to adjust motors 324, 428 until the concentration of hydrogen peroxide vapor in decontamination chamber 50B, as measured by sensor 552, is within the user-defined acceptable range. Similarly, controller 800 is programmed to adjust motor 324 and heater 342 until the airflow rate and the temperature of the air within decontamination chamber 50B is such that the concentration of hydrogen peroxide vapor in decontamination chamber 50B is within the user-defined acceptable range. Controller 800 is also programmed to adjust the speed of motor 16B such that containers 12 are exposed to hydrogen peroxide vapor for a duration of time sufficient to sterilize containers 12.

It is contemplated that controller 800 also may initiate the second mode of operation based upon an event indicative of a malfunction of conveyor 14A. In this respect, the event indicative of a malfunction may be a signal from sensor 564 that indicates that containers 12 have ceased to move through decontamination chamber 50A. Similarly, the event indicative of a malfunction may be a signal from sensor 562 that indicates that the speed of conveyor 14A is outside of an acceptable range. Based on the aforementioned signals, controller 800 is programmed to initiate the second mode of operation, as described above.

Controller 800 is also programmed to initiate the second mode of operation based upon a signal received from an operator. For example, an operator may send a signal to controller 800 that indicates that the first processing line is to be shut down. The command from the operator may be in response to a malfunction detected by the operator or because the operator wishes to perform maintenance on the first processing line. In either respect, based on the signal from the operator, controller 800 will initiate the second mode of operation to shut down the first processing line.

Regardless of the reasons the second mode of operation was initiated, controller 800 will continue to cause system 10 to operate in the second mode of operation until it is determined that the first processing line is ready to resume full operation. The operator then will send a signal to controller 800 to place the first processing line back into full operation. Based on the signal from the operator, controller 800 will cause valve 364A to move to the appropriate position and motor 16A to cause conveyor 14A to convey containers 12 through decontamination chamber 50A at the appropriate speed. Simultaneously therewith, controller 800 will control the components of vaporizer unit 300 to maintain the concentration of hydrogen peroxide vapor in both decontamination chambers 50A, 50B within the user-defined acceptable range. For example, controller 800 is programmed to cause motor 428 to increase or decrease the flow rate of liquid hydrogen peroxide to vaporizer 360 and to cause motor 324 to increase or decrease the flow rate of air to decontamination chambers 50A, 50B. Controller 800 will continue to adjust motors 324, 428 until the concentration of hydrogen peroxide vapor in decontamination chambers 50A, 50B is within the user-defined acceptable range. Similarly, controller 800 is programmed to adjust heater 342 until the air temperature in both decontamination chambers 50A, 50B is such that concentration of hydrogen peroxide vapor in each decontamination chamber is within the user-defined, acceptable range. As noted above, the speed at which containers 12 move along the first processing line is determined based on the concentration of hydrogen peroxide vapor in decontamination chamber 50A. The speed of containers 12 is selected to expose containers 12 to hydrogen peroxide vapor for a duration of time sufficient to sterilize containers 12.

According to another embodiment of the present invention, controller 800 is programmed to cause aeration unit 700 to stop or adjust the flow of air to the processing line associated with decontamination chamber 50A, during the second mode of operation. In this respect, controller 800 is programmed to adjust the position of valve 752A, as needed. Simultaneously therewith, controller 800 monitors sensors 734, 736, 766 in system 10. Based on the signals received from the foregoing sensors, controller 800 will control motor 714 to adjust the output of blower 712 so that the amount of air conveyed into decontamination chamber 50B remains within the user-defined acceptable range. For example, controller 800 is programmed such that, based on signals from sensor 766 in manifold 762, controller 800 determines if the temperature of the air supplied to decontamination chamber 50B is within the user-defined acceptable range. If the temperature of the air is outside of the user-defined acceptable range, controller 800 will increase or decrease the amount of heat generated by heater 744 to raise or lower the temperature of the air conveyed through decontamination chamber 50B. Similarly, controller 800 will adjust motor 714 until the amount of air flowing through decontamination chamber 50B is within the user-defined acceptable range.

The operation of system 10 during the second mode of operation was described above in reference to shutting down or modifying the operation of the first processing line. Similarly, controller 800 is programmed to shutdown or to modify the operation of the second processing line, while maintaining the first processing line in full operation.

System 10 has been described heretofore in reference to a system with two (2) processing lines. It is contemplated that system 10 may include more than two (2) processing lines wherein each processing line is connected to sterilant supply system 10. In this embodiment, controller 800 is programmed to monitor continuously a plurality of sensors associated with system 10. If an event indicative of a malfunction is detected with respect to one or more of the plurality of processing lines, controller 800 is programmed to adjust the operation of system 10 to maintain as many processing lines in full operation as possible. For example, based on the detected event, controller 800 may shut down one or more processing lines while maintaining uninterrupted operation of the remaining processing lines.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A system for conveying a sterilant vapor to a plurality of processing lines having articles moving therealong, said system comprised of:
   a single vaporizer unit for supplying a sterilant vapor;
   conveying means for conveying said sterilant vapor from said single vaporizer unit to a plurality of processing lines;
   sensing means for sensing a plurality of operational parameters associated with said system and said plurality of processing lines; and
   a controller for receiving signals from said sensing means, said controller programmed to operate in a first mode, wherein said controller monitors continuously said sensing means to determine if an event indicative of a malfunction has occurred with respect to said system or said plurality of processing lines, and said controller programmed to operate in a second mode in response to said event, wherein said controller adjusts the operation of said system to maintain uninterrupted operation of one or more of said plurality of processing lines.

2. A system as defined in claim 1, wherein said controller is programmed to adjust the output of said central source in response to said event.

3. A system as defined in claim 2, wherein said controller is programmed to adjust the concentration of said sterilant vapor supplied by said single vaporizer unit in response to said event.

4. A system as defined in claim 2, wherein said controller is programmed to adjust the temperature of said sterilant vapor supplied by said single vaporizer unit in response to said event.

5. A system as defined in claim 2, wherein said controller is programmed to adjust the flow rate of said sterilant vapor supplied by said single vaporizer unit in response to said event.

6. A system as defined in claim 1, wherein said controller is programmed to adjust selectively the concentration of said sterilant vapor supplied to each of said plurality of processing lines in response to said event.

7. A system as defined in claim 1, wherein said controller is programmed to adjust selectively the temperature of said sterilant vapor supplied to each of said plurality of processing lines in response to said event.

8. A system as defined in claim 1, wherein said controller is programmed to adjust selectively the flow rate of sterilant vapor supplied to each of said plurality of processing lines in response to said event.

9. A system as defined in claim 1, wherein said controller is programmed to adjust the operation of said plurality of processing lines in response to said event.

10. A system as defined in claim 9, wherein said controller is programmed to adjust the speed of said plurality of processing lines in response to said event.

11. A system as defined in claim 1, wherein said sensing means includes:
one conveyor sensor associated with one of said plurality of processing lines, said conveyor sensor operable to provide a signal indicative of the speed of said processing line associated with said conveyor sensor.

12. A system as defined in claim 11, wherein said event indicative of a malfunction with said system is a signal from said conveyor sensor that indicates that the speed at which said articles move along said one of said plurality of processing lines is outside of a user-defined acceptable range.

13. A system as defined in claim 1, wherein said sensing means includes:
one article sensor associated with one of said plurality of processing lines, said article sensor operable to provide a signal indicative of the presence of an article at a predetermined location along said processing line associated with said article sensor.

14. A system as defined in claim 13, wherein said event indicative of a malfunction with said system is a signal from said article sensor that indicates that the number of said articles moving along said one of said plurality of processing lines is outside of a user-defined acceptable range.

15. A system as defined in claim 1, wherein said sensing means includes:
one sterilant sensor associated with one of said plurality of processing lines, said sterilant sensor operable to provide a signal indicative of the concentration of said sterilant vapor at a discrete location along said processing line associated with said sterilant sensor.

16. A system as defined in claim 15, wherein said event indicative of a malfunction with said system is a signal from said sterilant sensor that indicates that the concentration of said sterilant vapor at said discrete location is outside of a user-defined acceptable range.

17. A system as defined in claim 1, wherein said sensing means includes:
one temperature sensor associated with one of said plurality of processing lines, said temperature sensor operable to provide a signal indicative of the temperature of said sterilant vapor at a discrete location along said processing line associated with said temperature sensor.

18. A system as defined in claim 17, wherein said event indicative of a malfunction with said system is a signal from said temperature sensor that indicates that the temperature of said sterilant vapor at said discrete location is outside of a user-defined acceptable range.

19. A system as defined in claim 1, wherein said sensing means includes:
one flow rate sensor associated with one of said plurality of processing lines, said flow rate sensor operable to provide a signal indicative of the flow rate of said sterilant vapor at a discrete location along said processing line associated with said flow rate sensor.

20. A system as defined in claim 19, wherein said event indicative of a malfunction with said system is a signal from said flow rate sensor that indicates that the flow rate of said sterilant vapor at said discrete location is outside of a user-defined acceptable range.

21. A system as defined in claim 1, wherein said single vaporizer unit includes:
a vaporizer connected to a sterilant supply unit for supplying uninterrupted flow of a liquid sterilant, said vaporizer for vaporizing said liquid sterilant; and
a first blower for conveying said sterilant vapor to a discrete location along each of said plurality of process lines.

22. A system as defined in claim 1, wherein said system further includes:
a plurality of conduits wherein each of said conduits extends from said single vaporizer unit to one of said plurality of processing lines, and
a valve disposed within each of said plurality of conduits for allowing said controller to independently control the flow of said sterilant vapor from said single vaporizer unit to each of said plurality of processing lines.

* * * * *